(12) United States Patent
Gross et al.

(10) Patent No.: US 7,582,053 B2
(45) Date of Patent: Sep. 1, 2009

(54) CONTROL OF URGE INCONTINENCE

(75) Inventors: Yossi Gross, Moshav Mazor (IL); Ehud Cohen, Ganei Tikva (IL); Israel Nissenkorn, Ramat Aviv (IL); David Lifschitz, Zurich (CH)

(73) Assignee: AMS Research Corporation, Minnetonka, MN (US)

( * ) Notice: Subject to any disclaimer, the term of this patent is extended or adjusted under 35 U.S.C. 154(b) by 773 days.

(21) Appl. No.: 10/671,144

(22) Filed: Sep. 24, 2003

(65) Prior Publication Data

US 2005/0261746 A1   Nov. 24, 2005

Related U.S. Application Data

(63) Continuation of application No. 09/806,970, filed as application No. PCT/IL99/00528 on Oct. 5, 1999, now Pat. No. 6,652,449, which is a continuation of application No. 09/167,244, filed on Oct. 6, 1998, now abandoned.

(51) Int. Cl.
*A61F 2/02* (2006.01)

(52) U.S. Cl. ............................................. 600/30

(58) Field of Classification Search ............ 600/29–32, 600/549, 551, 591; 128/DIG. 25; 607/70–72, 607/61, 41, 138
See application file for complete search history.

(56) References Cited

U.S. PATENT DOCUMENTS

| | | | |
|---|---|---|---|
| 3,628,538 A | 12/1971 | Vicent | |
| 3,640,284 A | 2/1972 | De Langis | |
| 3,662,758 A | 5/1972 | Eugene | |
| 3,866,613 A | 2/1975 | Kenney et al. | |
| 3,870,051 A | 3/1975 | Brindley | |
| 3,926,178 A | 12/1975 | Feldzamen | |
| 3,941,136 A | 3/1976 | Bucalo | |
| 3,983,865 A | 10/1976 | Shepard | |
| 3,983,881 A | 10/1976 | Wickham | |
| 4,023,574 A | 5/1977 | Nemec | |
| 4,106,511 A | 8/1978 | Erlandsson | |
| 4,136,684 A | 1/1979 | Scattergood et al. | |
| 4,139,006 A | 2/1979 | Corey | |
| 4,153,059 A | 5/1979 | Fravel et al. | |
| 4,157,087 A | 6/1979 | Miller et al. | |

(Continued)

FOREIGN PATENT DOCUMENTS

WO    WO 00/01320    1/2000

OTHER PUBLICATIONS

U.S. Appl. No. 60/091,762.

(Continued)

*Primary Examiner*—John P Lacyk
(74) *Attorney, Agent, or Firm*—Jose' W. Jimenez; Kimberly K. Baxter

(57) ABSTRACT

A device (20) for treatment of a patient's urinary incontinence, including a sensor, (44), which generates a signal responsive to a physiological characteristic indicative of a likelihood of incontinence. A control unit (22) receives the signal from the sensor. At least one electrode (29) is preferably implanted in the patient. The electrode is coupled to cause contraction of a pelvic muscle of the patient responsive to application of electrical energy to the electrode. Responsive to the signal, the control unit applies an electrical waveform to the electrode, so as to inhibit the incontinence.

17 Claims, 8 Drawing Sheets

U.S. PATENT DOCUMENTS

| | | | |
|---|---|---|---|
| 4,165,750 A | 8/1979 | Aleev et al. | |
| 4,177,819 A | 12/1979 | Kofsky et al. | |
| 4,222,377 A | 9/1980 | Burton | |
| 4,290,420 A | 9/1981 | Manetta | |
| 4,406,288 A | 9/1983 | Horwinski et al. | |
| 4,457,299 A | 7/1984 | Cornwell | |
| 4,492,233 A | 1/1985 | Petrofsky et al. | |
| 4,515,167 A | 5/1985 | Hochman | |
| 4,542,753 A | 9/1985 | Brenman et al. | |
| 4,568,339 A | 2/1986 | Steer | |
| 4,571,749 A | 2/1986 | Fischell | |
| 4,580,578 A | 4/1986 | Barsom | |
| 4,607,639 A | 8/1986 | Tanagho et al. | |
| 4,688,575 A | 8/1987 | DuVall | |
| 4,731,083 A | 3/1988 | Fischell | |
| 4,739,764 A | 4/1988 | Lue et al. | |
| 4,785,828 A | 11/1988 | Maurer | |
| 4,881,526 A | 11/1989 | Johnson et al. | |
| 5,103,835 A | 4/1992 | Yamada et al. | |
| 5,285,781 A | 2/1994 | Brodard | |
| 5,291,902 A | 3/1994 | Carman | |
| 5,411,548 A | 5/1995 | Carman et al. | |
| 5,423,329 A | 6/1995 | Ergas | |
| 5,452,719 A | 9/1995 | Eisman et al. | |
| 5,484,445 A | 1/1996 | Knuth | |
| 5,562,717 A | 10/1996 | Tippey et al. | |
| 5,807,397 A | 9/1998 | Barreras | |
| 5,978,712 A * | 11/1999 | Suda et al. | 607/41 |
| 6,061,596 A * | 5/2000 | Richmond et al. | 607/41 |
| 6,135,945 A | 10/2000 | Sultan | |
| 6,185,452 B1 | 2/2001 | Schulman et al. | |
| 6,354,991 B1 | 3/2002 | Gross et al. | |
| 6,658,297 B2 | 12/2003 | Loeb | |
| 6,735,474 B1 | 5/2004 | Loeb et al. | |
| 7,328,068 B2 | 2/2008 | Spinelli et al. | 607/39 |
| 2002/0055761 A1 | 5/2002 | Mann et al. | |
| 2003/0018365 A1 | 1/2003 | Loeb | |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0015205 A1 | 1/2004 | Whitehurst et al. | |
| 2004/0059392 A1 | 3/2004 | Parramon et al. | |

OTHER PUBLICATIONS

P.D., O'Donnell ed., Urinary Incontinence, Chap. 26, 1997, Mosby Publishers, St. Louis, MI pp. 197-2002.

Medtronic®'s InterStim Therapy for Urinary Control-Patient Stories, 1997, Medtronic, Inc., Spring Lake Park, MN, 2 pages (http://webprod1.medtronic.com/neuro/interstim/4Bsize.html).

Summary of Safety and Effectiveness of Medtronic® InterStim® Sacral Nerve Stimulation (SNS)TM System, Sep. 1997, Medtronic, Inc., Spring Lake Park, MN, 2 pages.

Medtronic®'s InterStim Therapy for Urinary . . . for People with Bladder Control Problem, 1997, Medtronic, Inc., Spring Lake Park, MN, 2 pages. (http://webprod1.medtronic.com/neuro/interstim/1types.html).

Caldwell, K.P.S. "Electrical Stimulation.", Sphincter Research Unit, Royal Devon and Exeter Hospital, Exeter (England), Urol. Int. 29: 225, 1974. (1 page).

Caldwell, K.P.S. "The Use of Electrical Stimulation in Urinary Retention and Incontinence [Abridged]." Section of Urology, vol. 61, pp. 35-39, Jul. 1968.

Caldwell, K.P.S. et al. "Urethral Pressure Recordings In Male Incontinents Under Electrical Stimulation." Investigative Urology vol. 5, No. 6, pp. 572-579, May 1968.

Caldwell, K.P.S. et al. "Stress Incontinence in Females: Report on 31 Cases Treated By Electrical Implant." J. Obstet. Gynaec. Brit. Cwlth vol. 75, pp. 777-780, Jul. 1968.

* cited by examiner

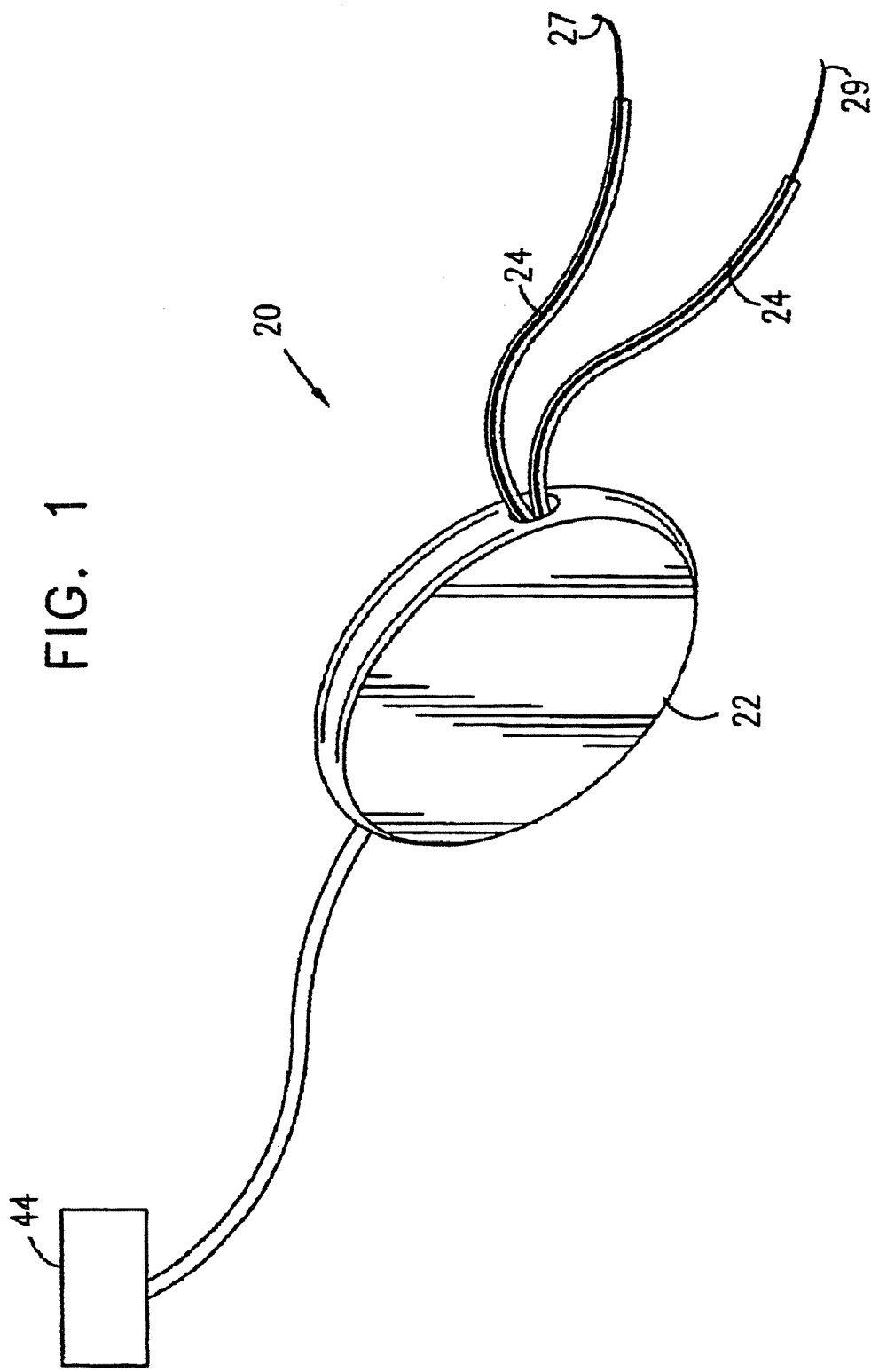

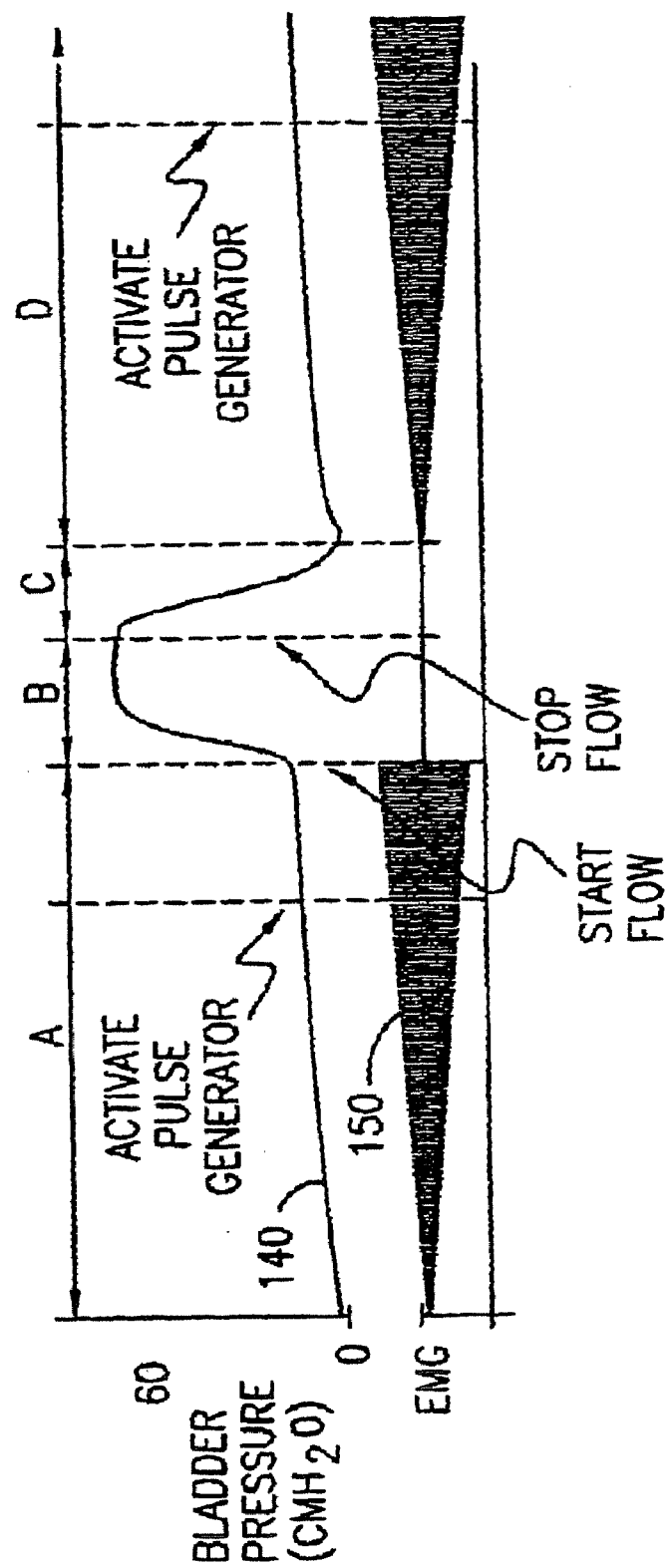

CONTROL OF URGE INCONTINENCE

This is a continuation of U.S. application Ser. No. 09/806,970, filed on Jul. 20, 2001, now U.S. Pat. No. 6,652,449, which was filed as a 35 U.S.C. §371 application of International Application No. PCT/IL99/00528, filed on Oct. 5, 1999, which is a continuation of U.S. application Ser. No. 09/167,244, filed on Oct. 6, 1998, now abandoned.

FIELD OF THE INVENTION

The present invention relates generally to medical electronic devices, and specify to implantable electrical devices for treatment of urge incontinence.

BACKGROUND OF THE INVENTION

Urinary incontinence affects millions of people, causing discomfort and embarrassment, sometimes to the point of social isolation. In the United States, it is estimated that 10-13 million patients seek medical care for incontinence each year.

Urge incontinence is a common type of urinary incontinence, in which a sudden, urgent need to pass urine causes involuntary urination before the patient can get to a toilet. Urge incontinence may be caused by damage to nerve pathways from the brain to the bladder or by psychosomatic factors, leading to involuntary bladder contraction. Urge and stress incontinence may also occur together, particularly in older women.

A large variety or products and treatment methods are available for personal and medical care of incontinence. Most patients suffering from mild to moderate incontinence use diapers or disposable absorbent pads. These products are not sufficiently absorbent to be effective in severe cases. They are uncomfortable to wear, and cause skin irritation, as well as unpleasant odors. Other non-surgical products for controlling incontinence include urethral inserts (or plugs), externally-worn adhesive patches, and drugs.

Exercise and behavior training are also effective in some cases in rehabilitating pelvic muscles and thus reducing or resolving incontinence. Patients are taught to perform Kegel exercises to strengthen their pelvic muscles, which may be combined with electrical stimulation of the pelvic floor. Electromyographic biofeedback may also be provided to give the patients an indication as to the effectiveness of their muscular exertions. But retraining muscles is not possible or fully effective for most patients, particularly when there may be neurological damage or when other pathologies may be involved.

Medtronic Neurological, of Columbia Heights, Minn., produces a device known as Interstim for treatment of urge incontinence. Interstim uses an implantable pulse generator, which is surgically implanted in the lower abdomen and wired to nerves near the sacrum (the bone at the base of the spine) in a major surgical procedure—sometimes six hours under general anesthesia. Electrical impulses are then transmitted continuously to a sacral nerve that controls urinary voiding. The continuous electrical stimulation of the nerve has been found to reduce or eliminate urge incontinence in some patients. The batteries in the pulse generator must be replaced every 5-10 years. The strength and frequency of nerve stimulation are programmable allowing the treatment to be tailored to the patient, and a hand-held programming device is available for this purpose.

U.S. Pat. No. 4,607,639, which is incorporated herein by reference, describes a method for controlling bladder function by nerve stimulation, typically of a sacral nerve. The anatomical location of at least one nerve controlling the muscles for the bladder and/or its sphincter is identified, and an electrode is placed on the nerve to selectively stimulate the nerve for continence and evacuation purposes. The electrode can be implanted in a patient either surgically or percutaneously and may be either removed after neurostimulation has achieved the desired result or may be left intact on the nerve for selective stimulation thereof. Further aspects and applications of these techniques are described in U.S. Pat. No. 4,739,764. U.S. Pat. No. 5,484,445 describes a system for anchoring a lead to the sacrum for purposes of long-term stimulation, typically for treatment of incontinence. Both of these patents are also incorporated herein by reference.

U.S. Pat. No. 3,628,538, which is incorporated herein by reference, describes apparatus for stimulating a muscle, using an electromyogram (EMG) signal sensed in the muscle. If the signal is greater than a threshold value, a stimulator circuit applies a voltage to electrodes adjacent to the muscle. The apparatus is said to be useful in overcoming incontinence.

Various types of electrodes have been proposed for applying electrical stimulation to pelvic muscles so as to prevent unwanted urine flow through the urethra. For example, U.S. Pat. No. 5,562,717 describes electrodes that are placed on the body surface, typically in the areas of the perineum and the sacrum, and are electrically actuated to control incontinence. U.S. Pat. No. 4,785,828 describes a vaginal plug having electrodes on an outer surface thereof. A pulse generator in the plug applies electrical pulses to the electrodes so as to constrict the pelvic muscles and prevent urine flow. U.S. Pat. No. 4,153,659 describes an intra-arm electrode, to which repetitive electrical pulses are applied in order to control urinary incontinence. U.S. Pat. No. 4,106,511 similarly describes an electrical stimulator in the form of a plug for insertion into the vagina or the anus. U.S. Pat. No. 3,866,613 describes a pessary ring having two electrodes thereon, which are energized control incontinence. All of the above-mentioned patents are incorporated herein by reference.

U.S. Pat. No. 4,580,578, which is also incorporated herein by reference, describes a device for stimulating the sphincter muscles controlling the bladder. A supporting body is fitted into the patient's vulva between the labia, so that two electrodes attached to the supporting body contact the epidermal surface on either side of the external urethral orifice. Electrical impulses are applied to the electrodes to stimulate the region of the sphincter.

A book entitled *Urinary Incontinence*, edited by P. O'Donnell Mosby Publishers, 1997, which is incorporated herein by reference, describes clinical aspects relating to the diagnosis and a treatment of urinary incontinence.

SUMMARY OF THE INVENTION

It is an object of some aspects of the present invention to provide an improved device and method of treatment for incontinence, particularly urinary urge incontinence.

It is a further object of some aspects of the present invention to provide a device and method for enhancing function of muscles, particularly those associated with urine control.

In preferred embodiments of the present invention, a device for treatment of urinary incontinence comprises a control unit, one or more electrodes coupled to the control unit, and one or more optional sensors, also coupled to the control unit. Typically, but not necessarily, the device is used to treat urge incontinence, The electrode or electrodes are preferably implanted in the pelvic region of a patient so as to contact the one Or more of the muscles or nerves that are used in regulating urine flow from the bladder. The control unit is preferably implanted under the skin of the abdomen or genital region, and receives signals from the electrodes and/or from the sensors. When the control unit determines that the signals are indicative of impending involuntary uriae flow from the bladder, it applies a suitable electrical waveform to the electrode or electrodes, stimulating the contacted muscle or nerve to inhibit the urine flow.

In some preferred embodiments of the present invention, the electrodes are coupled to sense electromyogram (EMG) signals and/or to apply electrical stimulation to the detrusor muscle. The detrusor is responsible for bladder contraction and is believed to have a major role in causing, as well as relieving, urge incontinence. Although Medtronic's Interstim nerve stimulator attempts to regulate detrusor contraction, it requires costly, major abdominal surgery for implantation. Preferred embodiments of the present invention offer a solution that is less invasive and lower in cost. Typically, in contrast to the Interstim stimulator, devices in accordance with preferred embodiments of the present invention actuate the electrodes to mediate urge incontinence only when physiological signals indicate that such mediation is needed. Numerous benefits are accrued, according to these embodiments, by actuating the electrodes only "on-demand," i.e., only when possible imminent incontinence is detected. For example, muscle fatigue and nerve irritation—both phenomena being associated with continuous excitation—are reduced or eliminated affording to these embodiments. Additionally, power consumption is reduced, and battery life is thereby increased by limiting the electrical power output of the stimulator. Further, additionally, safety may be increased, by decreasing the time during which possibly errant stimulation might cause a pelvic or non-pelvic muscle to contract inappropriately. In other preferred embodiments of the present invention, however, the device may be configured to provide continuous stimulation.

Preferably, the electrodes are implanted so as to stimulate muscles of the pelvic floor. Alternatively or additionally, one or more of the electrodes may be implanted in or adjacent to the detrusor muscle or in a position suitable for stimulating a nerve, such as the sacral nerve, which controls detrusor function, as described in the above-mentioned U.S. Pat. No. 4,607,639, for example.

In some preferred embodiments of the present invention, the one or more electrodes comprise a single electrode, which both receives the EMG signals and applies the stimulation waveform. Alternatively, separate sensing and stimulation electrodes may be used.

In further preferred embodiments of the present invention, the sensors comprise one or more physiological sensors, such as pressure, force, motion or acceleration sensors, or an ultrasound transducer, which are preferably implanted on, in or in the vicinity of the bladder. The other sensors generate signals responsive to motion or to intravesical or abdominal pressure, or to urine volume in the bladder. These signals are thus indicative of possible incontinence. On the other hand, when the urine volume in the bladder is low, there will be no urine flow even when the abdominal pressure does increase. The control unit processes the signals from the other sensors and uses them to determine when the electrical stimulation should be applied.

Preferably, the control unit comprises a processor, which is programmed to distinguish between signals indicative of possible incontinence and other signals that do not warrant stimulation of the muscles. In particular, the processor is programmed to recognize signal patterns indicative of normal voicing, and does not stimulate the muscles when such patterns occur, so that the patient can pass urine normally. Preferably, in order to reduce consumption of electrical power, the control unit comprises a low-power, tow-speed processor, which monitors the EMG sisals continuously, and a high-speed processor, which turns on only when the low-speed portion detects an increase in EMG activity. The high-speed portion performs an accurate analysis of the signals to determine whether stimulation is actually warranted.

In a preferred embodiment of the present invention, the processor is programmable after implantation of the device, most preferably by means of a wireless communications link, so that the strength and shape of the stimulation waveform and the response of the device to the electromyographic and/or other physiological signals can be adjusted to response to the patient's clinical characteristics and experience with the device. The wireless link can also be used by the patient to turn the device on or off. Such methods of signal processing, programming and control, as well as other useful methods and apparatus, are described in a U.S. patent application entitled "Incontinence Treatment Device," which is assigned to the assignee of the present patent application and is incorporated herein by reference.

Although preferred embodiments of the present invention are described with reference to treatment of urinary incontinence, particularly urge incontinence, it will be appreciated that the principles of the present invention may be applied as well to treat other types of incontinence, such as fecal incontinence, and to treat and enhance the function of other muscles in the body. Alternatively or additionally, principles of the present invention may be applied to treating constipation or pathological retention of urine, typically by stimulating some muscles to contract (e.g. muscles of the colon), while stimulating some parasympathetic nerves to induce relaxation of other muscles (e.g., the muscles of the anus). These applications of the invention may be particularly useful following spinal cord injury.

There is therefore provided, in accordance with a preferred embodiment of the present invention, a device for treatment of urinary incontinence, including:

a sensor, which generates a signal responsive to a physiological characteristic indicative of a likelihood of inconvenience;

a control unit, which receives the signal from the sensor; and at least one electrode, implanted in a patient and coupled to cause contraction of a pelvic muscle of the patient responsive to application of electrical emergency to the electrode, to which electrode the control unit applies an electrical waveform responsive to the signal so as to inhibit the incontinence.

In a preferred embodiment, the control unit analyzes the sensor signal to determine a time of voiding, and applies the electrical waveform at a designated time interval subsequent to the time of voiding.

Preferably, the urinary incontinence includes urinary urge incontinence.

In a preferred embodiment, the control unit is implanted in a vicinity of the patient's sacral spine.

Preferably, the electrode is implanted in the pelvic muscle of the patient. Further preferably, the pelvic muscle includes a pelvic Poor muscle. Most preferably, the pelvic muscle includes the levator ani muscle or the urethral sphincter muscle, or, alternatively, the pelvic muscle is adjacent to the urethral sphincter muscle.

In a preferred embodiment, the electrode includes a single unipolar electrode or a pair of bipolar electrodes. Alternatively or additionally, the electrode includes a flexible intramuscular electrode.

Preferably, the control unit receives data indicative of a fill level of the patient's bladder and, responsive to the data, does not apply the electrical waveform when the fill level of the bladder is low, even when the signal generated by the sensor is indicative of involuntary urination.

In a preferred embodiment, the sensor includes a pressure sensor, an acceleration sensor, and/or an ultrasound transducer.

In a preferred embodiment, the electrode is electrically coupled to a nerve which innervates the pelvic muscle.

Preferably, the sensor includes a detecting electrode, and the signal includes an electromyographic (EMG) signal generated by the detecting electrode. In a preferred embodiment, the control unit applies the electrical waveform responsive to an average magnitude of the EMG signal, preferably responsive to the average magnitude of the EMG signal exceeding a designated threshold.

Preferably, the at least one electrode includes a detecting electrode, and the sensor includes the detecting electrode. In a preferred embodiment, the device includes a switch between the detecting electrode and an input of the control unit, which switch is opened when the electrical waveform is applied so as to prevent feedback from the detecting electrode to the input.

In a preferred embodiment, the electrode is electrically coupled to a nerve which innervates the pelvic muscle. Preferably, the nerve includes a sacral nerve.

Preferably, the control unit is implanted in the body of the patient and includes a rechargeable power source. In a preferred embodiment, the power source is recharged by inductive energy transfer, substantially without requiring electrical contact between the control unit and any object outside the patient's body.

Further preferably, the control unit includes a processor, which analyzes the signal so as to determine when an involuntary urine flow is likely, whereupon the waveform is applied. In a preferred embodiment, the processor analyzes The signal at a sample rate substantially greater than 1000 Hz. Preferably, the processor's analysis uses spectral analysis, and is performed on substantially non-rectified data.

Still further preferably, the processor is programmable to vary one or more parameters associated with the application of the waveform. In a preferred embodiment, the device includes a wireless receiver, which receives data for programming the processor from a programming unit outside the patient's body.

Preferably, the processor includes a first processor, which analyzes the signal substantially continuously at a low data analysis rate, and a second processor, which is actuated by the first processor to analyze the signal at a high data analysis rate when the first processor determines that involuntary urine flow is likely to occur. Further preferably, the device includes a queue, in which the signal is stored before the second processor is actuated, and from which queue the signal received by the control unit prior to actuation of the second processor is passed to the second processor for analysis.

Preferably, the processor distinguishes between a signal indicative of an involuntary urine flow and a signal indicative of voluntary voiding by the patient. In a preferred embodiment, the processor distinguishes between the signal indicative of involuntary urine flow and the signal indicative of voluntary voiding by the patient responsive to a rate of change of the signal generated by the sensor.

In a preferred embodiment, the processor gathers information regarding the signal over an extended period and analyzes the information to find a pattern characteristic of the patient, for use in determining when an involuntary urine flow is likely. The pattern may include a time-varying threshold to which a level of the signal is compared.

There is further provided, in accordance with a preferred embodiment of the present invention, a device for treatment of urinary incontinence in a patient, including:

a sensor, which is coupled to generate a signal responsive to a fill level of the patient's bladder; and a control unit, which receives and analyzes the signal so as to determine a fill level of the bladder and, responsive to the determination, applies electrical stimulation to cause the contraction of a pelvic muscle of the patient, so as to inhibit the urinary incontinence when the fill level of the bladder is above a threshold level.

Preferably, the incontinence includes urge incontinence. Alternatively or additionally, the incontinence includes stress incontinence.

Preferably, the device includes an electrode, which is placed in electrical contact with a nerve which innervates the pelvic muscle, and the stimulation includes an electrical waveform applied to the electrode so as to stimulate the nerve to cause the muscle to contract, thereby inhibiting the incontinence. Alternatively or additionally, the device includes an electrode, which is placed in electrical contact with the pelvic muscle or the patient, wherein the stimulation includes an electrical waveform applied to the electrode so as to stimulate the muscle to contract, thereby inhibiting the incontinence.

Preferably, the control unit receives a signal indicative of a likelihood of involuntary urination and applies the stimulation to the pelvic muscle responsive to the likelihood except when the fill level of the bladder is below the threshold level. In a preferred embodiment, the sensor includes an electrode, which is placed in electrical contact with the pelvic muscle of the patient to receive an electromyogram signal therefrom indicative of the likelihood of involuntary urination and of the fill level.

There is still further provided, in accordance with a preferred embodiment of the present invention, a device for treatment of urinary incontinence, including:

at least one electrode, which is coupled to a pelvic muscle of a patient; and a control unit, which receives electromyogram signals from the electrode indicative of possible imminent incontinence, and which determines a threshold signal level that varies over time responsive to a condition of the patient, and which, responsive to a transient increase in the electromyogram signal above the threshold level, applies an electrical waveform to stimulate the muscle to contract, so as to inhibit the incontinence.

Preferably, the control unit applies the waveform to the electrode.

In a preferred embodiment, the device includes a second electrode, coupled to a nerve which innervates the pelvic muscle, and the control unit applies the waveform to the second electrode to cause contraction of the muscle.

Preferably, the threshold signal level varies over time responsive to temporal variation of a mean value of the electromyogram signal. Alternatively or additionally, the threshold signal level increases responsive to time elapsed since the patient last passed urine. Further alternatively or additionally, the threshold signal level increases responsive to an increase in a fill level of the patient's bladder.

There is yet further provided, in accordance with a preferred embodiment of the present invention, a device for treatment of urinary incontinence, including:

at least one electrode, which is placed in electrical contact with the pelvic muscle of a patient; and a control unit, which receives electromyogram signals from the electrode and, responsive to a rate of change of the signals indicative of possible imminent incontinence, applies an electrical waveform which stimulates the muscle to contract, so as to inhibit the incontinence.

Preferably, when the rate of change is below a threshold rate, the control unit withholds the waveform, so as to allow voluntary voiding.

There is also provided, in accordance with a preferred embodiment of the present invention, a device for treatment of urinary incontinence, including:

at least one electrode, which is placed in electrical contact with a pelvic muscle of a patient, and a control unit, which receives signals indicative of impending urine flow, and distinguishes signals indicative of possible imminent incontinence from signals indicative of voluntary voiding by the patient, and responsive thereto applies an electrical waveform to the electrode which stimulates the muscle to contract, so as to inhibit incontinence.

In a preferred embodiment, the control unit distinguishes between the signals indicative of incontinence and the signals indicative of voluntary voiding by the patient responsive to a rate of change of the received signals.

Preferably, the control unit distinguishes between the signals indicative of incontinence and the signals indicative of voluntary voiding, substantially without application of an input to the control unit from outside the patient's body.

In a preferred embodiment, the control unit gathers information regarding the signals over an extended period and analyzes the information to find a pattern characteristic of the patient, for use in determining when incontinence is likely. Preferably, the pattern includes a time-varying threshold to which a level of the signals is compared.

There is additionally provided, in accordance with a preferred embodiment of the present invention, a device for treatment of urinary incontinence, including:

at least one electrode, coupled to cause contraction of a pelvic muscle of a patient responsive to application of electrical energy to the electrode; and a control unit, which receives at a sample rate substantially greater than 1000 Hz signals indicative of possible imminent incontinence, analyzes the signals so as to determine when the incontinence is likely, and, responsive thereto, applies an electrical waveform to the electrode which causes the muscle to contract, so as to inhibit the incontinence.

There is still additionally provided, in accordance with a preferred embodiment of the present invention, a device for treatment of urinary incontinence, including:

at least one electrode, coupled to cause contraction of a pelvic muscle of a patient responsive to application of electrical energy to the electrode;

a first processor, which receives signals indicative of a likelihood of imminent incontinence and analyzes the signals substantially continuously at a low data analysis rate; and a second processor, which, responsive to a determination by the first processor that incontinence is imminent, is actuated by the first processor to analyze the signals at a high data analysis rate and, responsive to the analysis at the high data rate, applies an electrical waveform to the electrode which stimulates the muscle to contract, so as to inhibit the incontinence.

Preferably, the device includes a queue, in which the signals are stored before the second processor is actuated, and from which queue signals received by the first processor prior to actuation of the second processor are passed to the second processor for analysis.

There is yet additionally provided, in accordance with a preferred embodiment of the present invention, a method for treatment of urinary incontinence, including:

coupling an electrode to cause contraction of a pelvic muscle of a patient responsive to application of electrical energy to the electrode;

receiving a signal from the patient's body indicative of impending urine flow;

analyzing the received signal to distinguish between a signal indicating that incontinence is likely and another signal indicative of voluntary voiding; and responsive to the analysis, applying, an electrical waveform to the electrode, which stimulates the muscle to contract so as to inhibit incontinence.

In a preferred embodiment, distinguishing between the signals includes gathering information regarding the received signal over an extended period and analyzing the information to detect a pattern characteristic of the patient, for use in determining when incontinence is likely. In a preferred embodiment, the patient includes a time-varying threshold to which a level of the received signal is compared.

There is further provided, in accordance with a preferred embodiment of the present invention, a method for treatment of urinary incontinence, including:

coupling an electrode to cause contraction of a pelvic muscle of a patient responsive to application of electrical energy to the electrode;

receiving at a sample rate substantially greater than 1000 Hz signals indicative of imminent urination;

analyzing the signals so as to determine when incontinence is likely; and responsive to the analysis, applying an electrical waveform to the electrode, which stimulates the muscles to contract so as to inhibit incontinence.

Preferably, analyzing includes distinguishing between a signal indicating that involuntary urine flow is likely and another signal indicative of voluntary voiding.

There is still further provided, in accordance with a preferred embodiment of the present invention, a method for treatment of urinary stress incontinence of a patient, including:

implanting an electrode so as to cause contraction of a pelvic muscle of a patient responsive to application of electrical energy to the electrode;

receiving a signal from the patient's body indicative of imminent incontinence; and responsive to the signal, applying an electrical waveform to the electrode, which stimulates the muscle to contract so as to inhibit incontinence.

In a preferred embodiment, implanting the electrode includes implanting the electrode in the pelvic muscle. Alternatively or additionally, implanting the electrode includes implanting an electrode in proximity to the urethral sphincter muscle.

Preferably, applying the waveform includes varying a parameter of the waveform selected from the group consisting of amplitude, frequency, duration, wave shape and duty cycle. Alternatively or additionally, applying the waveform includes applying a pulse burst. Further alternatively or additionally, applying the waveform includes applying a waveform to the electrode in a unipolar mode. Still further alternatively or additionally, implanting the electrode includes placing at least two electrodes in electrical contact with the muscle, and applying the waveform includes applying a waveform between the electrodes in a bipolar mode.

In a preferred embodiment, receiving the signal includes receiving a signal indicative of pressure on the patient's bladder and/or indicative of motion of the patient's bladder.

Preferably, receiving the signal includes receiving an electromyographic (EMG) signal.

Further preferably, the method includes determining a time of voiding, wherein applying the electrical waveform includes applying the waveform at a designated time interval subsequent to the time of voiding.

In a preferred embodiment, implanting the electrode includes coupling the electrode to a nerve which innervates the pelvic muscle. Preferably, the nerve includes a sacral nerve.

Preferably, the method includes receiving a signal indicative of a fill level of the patient's bladder, wherein applying the electrical waveform includes applying a waveform responsive to the fill level. Further preferably, applying the waveform responsive to the fill level includes withholding application of the waveform when the fill level is low, notwithstanding the signal received indicative of abdominal stress.

There is still further provided, in accordance with a preferred embodiment of the present invention, a method for treatment of urinary incontinence, including:

receiving a signal indicative of a fill level of a patient's bladder; and applying stimulation to a pelvic muscle of the patient when the fill level of the bladder is above a threshold level, so as to inhibit incontinence.

Preferably, applying the stimulation includes applying an electrical waveform to an electrode in contact with the pelvic muscle, thereby stimulating the muscle to contract and inhibiting incontinence.

In a preferred embodiment, the method includes receiving a further signal indicative of a likelihood of imminent incontinence, wherein applying the stimulation includes applying stimulation responsive to the likelihood except when the fill level of the bladder is below the threshold level. Preferably, receiving the signal includes receiving an electromyogram signal from an electrode in contact with the pelvic muscle, wherein the signal is indicative of the likelihood of imminent incontinence and of the fill level.

There is yet further provided, in accordance with a preferred embodiment of the present invention, a method for treatment of urinary incontinence, including:

coupling an electrode to cause contraction of a pelvic muscle of a patient responsive to application of electrical energy to the electrode;

receiving electromyogram signals from the electrode indicative of a likelihood of imminent incontinence;

determining a threshold level of the signals that varies over time responsive to a condition of the patient; and responsive to a transient increase in the signals above the threshold level, applying an electrical waveform to the electrode which stimulates the muscle to contract, so as to inhibit incontinence.

In a preferred embodiment, determining the threshold level includes determining a level that varies over time responsive to temporal variation of a mean value of the electromyogram signals. Alternatively or additionally, determining the threshold level includes increasing the threshold level responsive to time elapsed since the patient last passed urine. Further alternatively or additionally, determining the threshold level includes increasing the threshold level responsive to an increase in a fill level of the patient's bladder.

There is also provided, in accordance with a preferred embodiment of the present invention, a method for treatment of urinary incontinence, including:

coupling an electrode to cause contraction of a pelvic muscle of a patient responsive to application of electrical energy to the electrode;

receiving electromyogram signals from the electrode indicative of a likelihood of imminent incontinence;

determining a rate of change of the signals; and responsive to the rare of change, applying an electrical waveform to the electrode which stimulates the muscle to contract, so as to inhibit incontinence.

Preferably, applying the waveform includes applying a waveform when the rare of change is above a threshold rate, and includes withholding the waveform when the rare of change is below the threshold rate, so as to allow voluntary voiding.

The present invention will be more fully understood from the following detailed description or the preferred embodiments thereof, taken together with the drawings in which:

BRIEF DESCRIPTION OF THE DRAWINGS

FIG. 1 is a schematic, pictorial view of an implantable device for prevention of urge incontinence, in accordance with a preferred embodiment of the present invention;

FIGS. 6, 7, and 8 are graphs showing simulated and measured signals, representative of different aspects of use of an implantable muscle stimulation device, in accordance with a preferred embodiment of the present invention.

DETAILED DESCRIPTION OF PREFERRED EMBODIMENTS

Figure 2A:
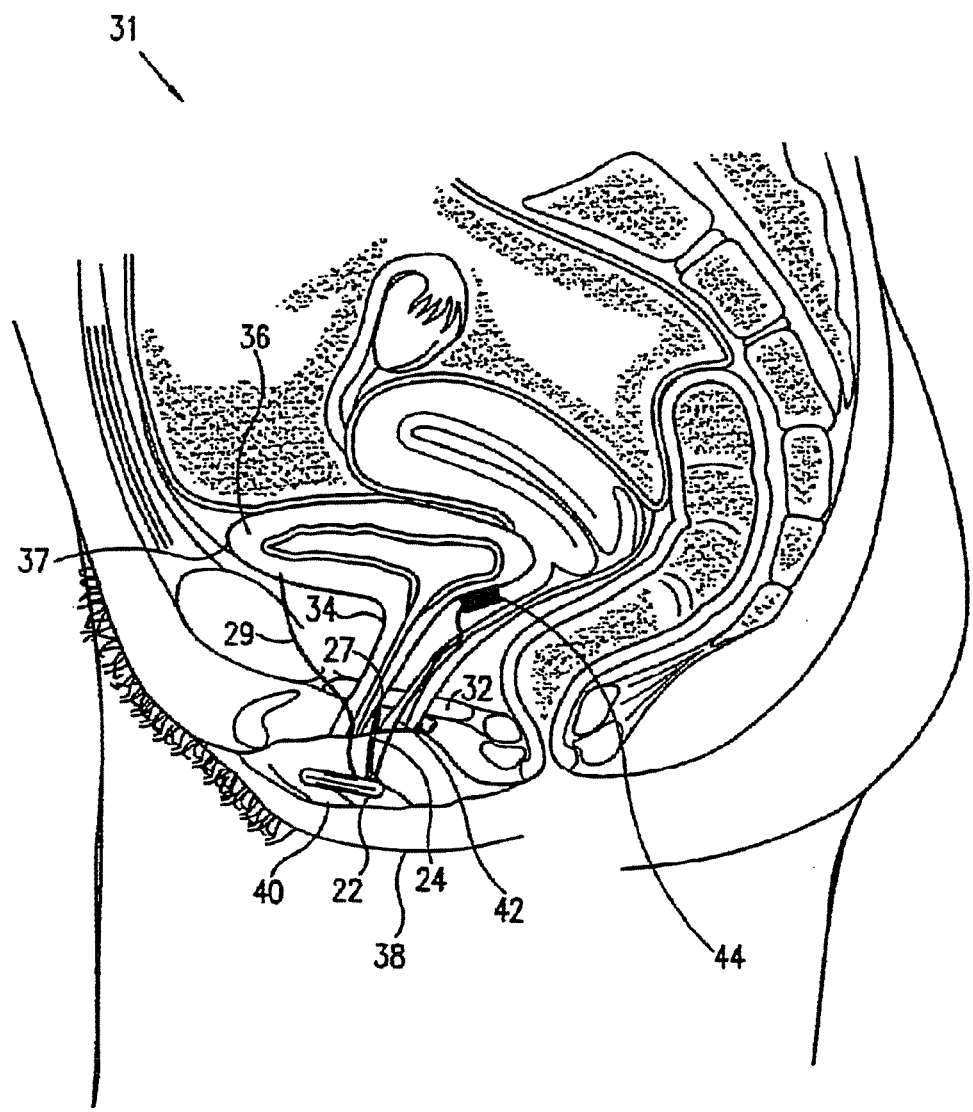
FIG. 2A is a schematic, partly sectional illustration showing implantation of the device of FIG. 1 in the pelvis of a patient, in accordance with a preferred embodiment of the present invention.

I. Overview of Preferred Embodiments
   A. General description of stimulator device
   B. Sensing and control functions of the device
   C. Signal processing
   D. Power consumption control II. Detailed Description of Figures
   A. External elements of a stimulator device
   B. Anatomical and surgical considerations
   C. Signal processing
     (i) hardware and algorithms
     (ii) stimulation of a typical EMG
     (iii) experimentally measured EMG signals: distinguishing incontinence from voluntary voiding
   D. Muscle stimulation
   E. Provision of power to the control unit
   F. External communication with the control unit
   G. Utilization of other sensors
   H. Reduction of power consumption

I. Overview of Preferred Embodiments

A. General Description of Stimulator Device

Various aspects of the present invention are described in this section (I) and in greater detail in the following section (II). As described with reference to the preferred embodiment shown in FIG. 1, an electronic stimulator device is preferably implanted in the genital region of a patient and stimulates one or more of the muscles or nerves in the region, so as to control and treat urinary incontinence, typically urge incontinence. Preferably, imminent urge incontinence generates an electromyographic (EMG) signal in the muscles, which is sensed by one or more electrodes and is analyzed by a control unit of the device. Alternatively or additionally, non-electromyographic signals are received and analyzed by the control unit. When the control unit determines that the signals are indicative of a condition, such as an increase in abdominal or intravesical pressure that is likely to cause involuntary urine flow from the bladder, it applies an electrical waveform to the one or more electrodes, to stimulate a pelvic muscle to contract and thus to inhibit the urine flow.

B. Sensing and Control Functions of the Device

In addition to EMG sensing electrodes, the device preferably also comprises one or more other physiological sensors, described hereinbelow with reference to FIGS. 2A, 2B, 3, and 4, which generate signals responsive to, for example, motion, intravesical or abdominal pressure, or urine volume in the bladder. These signals are indicative of some forms of incontinence. Typically, when the urine volume in the bladder is low, there will be no wine flow even when the abdominal pressure does increase. As described with reference to a plurality or the figures, the control unit preferably processes the signals from the other sensors and uses them to determine when the electrical stimulation should be applied to the muscles.

C. Signal Processing

Preferably, the control unit comprises a processor, e.g., as described with reference to FIGS. 3 and 4, which is programmed to distinguish between signals indicative of possible incontinence and other signals that do not warrant simulation of a nerve or muscle. In particular, the processor is preferably programmed to recognize signal patterns indicative of normal voiding, and does not stimulate the muscles when such patterns occur, so that the patient can pass urine normally. Detection of normal voiding is described in more detail with reference to FIGS. 7 and 8. Preferably, the processor analyzes both long-term and short-term variations in the signals, as well as rates, spectral patterns, and patterns of change in the signals. Most preferably, in response to the analysis, the processor sets a threshold of an aspect of the EMG signal that varies over time responsive to an assessment of the patient's physiological condition, and applies the stimulation only when a transient variation in the aspect of the EMG signal exceeds the threshold. Methods for modifying the threshold in real time are described with reference to FIG. 6.

In the context of the present patent application and in the claims, a "time-varying threshold" is to be understood as comprising substantially any appropriate time-varying detection parameters that a person skilled in the art, having read the disclosure of the present patent application, would consider useful in applying the principles of the present invention. By way of illustration and not limitation, these time-varying detection parameters may include magnitude, rate, or other aspects of the EMG signal, and quantitative ultrasound, pressure, or acceleration measurements, as described herein.

D. Power Consumption Control

As described with reference to FIG. 5, the control unit preferably comprises a low-power, low-speed processor, which monitors the EMG and/or sensor signals continuously, and a high-speed processor, which turns on only when the low-speed processor detects an increase in EMG or other activity. Use of the two processors has been shown to significantly reduce consumption of electrical power. The high-speed processor performs an accurate analysis of the signals to determine whether stimulation is actually warranted.

II. Detailed Description of Figures

A. External Elements of a Stimulator Device

Reference is now made to FIG. 1, which is a schematic, pictorial illustration of an implantable electronic stimulator device 20, in accordance with a preferred embodiment of the present invention. Device 20 is preferably implanted in the pelvic region of a patient, as described further hereinbelow, for use in providing muscle and/or nerve stimulation so as to control and treat urinary urge incontinence.

Device 20 comprises a control unit 22 and electrodes 27 and 29, coupled thereto by electrical leads 24. Additionally, device 20 optionally comprises at least one additional physiological sensor 44, such as a miniature ultrasound transducer, one or more accelerometers, a pressure transducer or other sensors known in the art. The control unit preferably comprises circuitry for sensing electrical signals received by electrodes 27 and 29, such as electromyogram (EMG) signals, along with signals from sensor 44. Control unit 22 additionally comprises circuitry for applying electrical stimulation waveforms to one or both of the electrodes responsive to the signals. Details of control unit 22 and electrodes 27 and 29 are preferably as described in the above-mentioned patent application entitled "Incontinence Treatment Device," with appropriate changes as described hereinbelow or as are otherwise indicated by clinical and engineering considerations that will be clear to those skilled in the art.

The electrodes are preferably flexible intramuscular-type wire electrodes, about 1-5 mm long and 50-100 microns in diameter, thus designed to minimize patient discomfort. They are typically formed in the shape of a spiral or hook, as is known in the art, so that they can be easily and permanently anchored in the muscle. The wire from which the electrodes are made comprises a suitable conductive material, preferably a biocompatible metal such as silver, a platinum/iridium alloy (90/10) or a nickel/chromium alloy. Lead 24 is preferably 5-10 cm long and has an insulating jacket preferably comprising nylon, polyurethane, Teflon or other flexible, biocompatible insulating material. An optional additional wire (not shown) inside the jacket serves as an antenna for the purpose of wireless communications wire device 20, as described further hereinbelow.

Control unit 22 preferably contains circuitry, described further hereinbelow with references to FIGS. 3, 4, and 5, for receiving electrical signals from and applying a waveform to electrodes 27 and 29 via lead 24. The circuitry is preferably contained in a case, made of stainless steel or other suitable biocompatible metal, and is preferably about 20 mm in diameter and 4 mm thick. For some applications, the stainless steel case serves as a ground electrode for electrodes 27 and 29 when they are sensing or stimulating in a bipolar mode. Alternatively, the case may be made of a plastic material which is coated with a layer of biocompatible plastic, such as polymethyl methacrylate (PMMA) or silicone. Although two electrodes and one sensor are shown attached to the control unit in FIG. 1, it is possible to use only a single electrode or, alternatively, additional electrodes and/or other sensors, as described further hereinbelow.

B. Anatomical and Surgical Considerations

FIG. 2A is a schematic, partly sectional illustration showing the genitourinary anatomy of a female patient 31 in whom device 20 is implanted, in accordance with a preferred embodiment of the present invention. It will be understood that, with appropriate changes, device 20 may be implanted in or coupled to a male patient. In this embodiment, electrode 27 is inserted into a muscle 32, such as the levator ani muscle, in a vicinity of urethra 34 and bladder 36. Electrode 29 is inserted into the patient's detrusor muscle 37, which surrounds bladder 36. Alternatively or additionally, electrodes 27 and 29, or additional electrodes not shown in the figure, may be placed in other muscles of the pelvic floor.

The precise placement of the electrodes is typically not essential, particularly since electrical signals tend to pass among the different muscles in the region. Thus, any placement of the electrode in or on one or more of the pelvic muscles suitable for exercising urine control is considered to be within the scope of this embodiment of the present invention. The electrodes are preferably inserted through an incision made in the wall of vagina 42. Alternatively, another suitable approach may be chosen for ease of access and minimization of tissue trauma.

Control unit 22 is preferably implanted under the skin in the genitopelvic region of patient 31. Most preferably, the control unit is implanted inside the patient's labia minora 38 or in the labia majora 40. Alternatively, the control unit is not implanted in the patient's body, but is instead maintained outside the body, connected by leads 24 to the electrodes. This configuration is convenient particularly for an initial test period, during which the effectiveness of device 20 in treating a given patient is evaluated before permanent implantation.

Figure 2B:
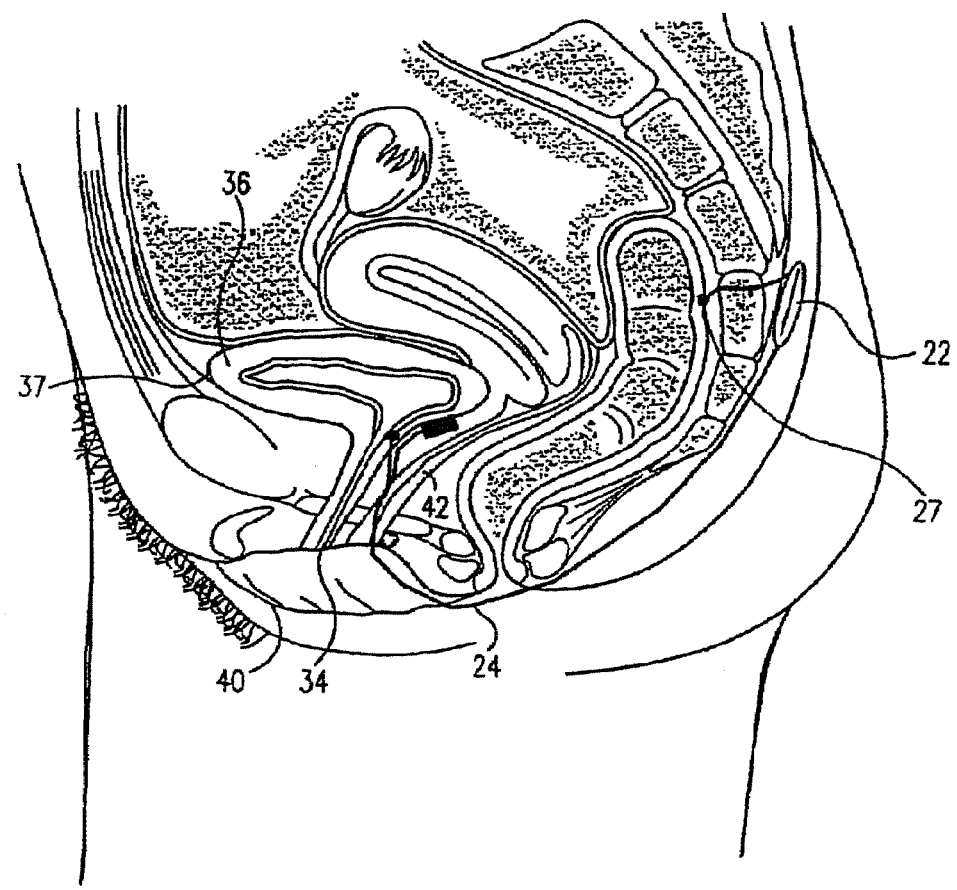
FIG. 2B is a schematic, partly sectional illustration showing implantation of the device of FIG. 1 in the pelvis of a patient, in accordance with another preferred embodiment of the present invention.

FIG. 2B is a schematic, partly sectional illustration showing the genitourinary anatomy of patient 31 in whom device 20 is implanted, in accordance with another preferred embodiment of the present invention. Preferably, control unit 22 is implanted in a vicinity of the sacral spine, as shown, but may alternatively be implanted in the abdomen or in the pelvis. According to this embodiment, the control unit drives electrode 27 to stimulate a nerve that innervates one or more muscles which are responsible for urine control. Typically, a sacral nerve is stimulated, so as to control the flow of urine from the bladder.

Generally, the choice of implantation location for the control unit, as well as which particular nerve is to be stimulated, is made by the patient's physician, responsive to the patient's condition and other surgical considerations. Preferably, electrode 29 (FIG. 2A), is implanted in the detrusor muscle or in another pelvic muscle, and provides EMG signals for analysis by the control unit. Further preferably, as described hereinbelow, electrode 29 conveys to the control unit EMG signals responsive to bladder contractions associated with imminent urge incontinence, whereupon the control unit drives electrode 27 to stimulate the sacral nerve and drives electrode 29 to stimulate the pelvic muscle.

C. Signal Processing (i) Hardware and Algorithms

Figure 3:
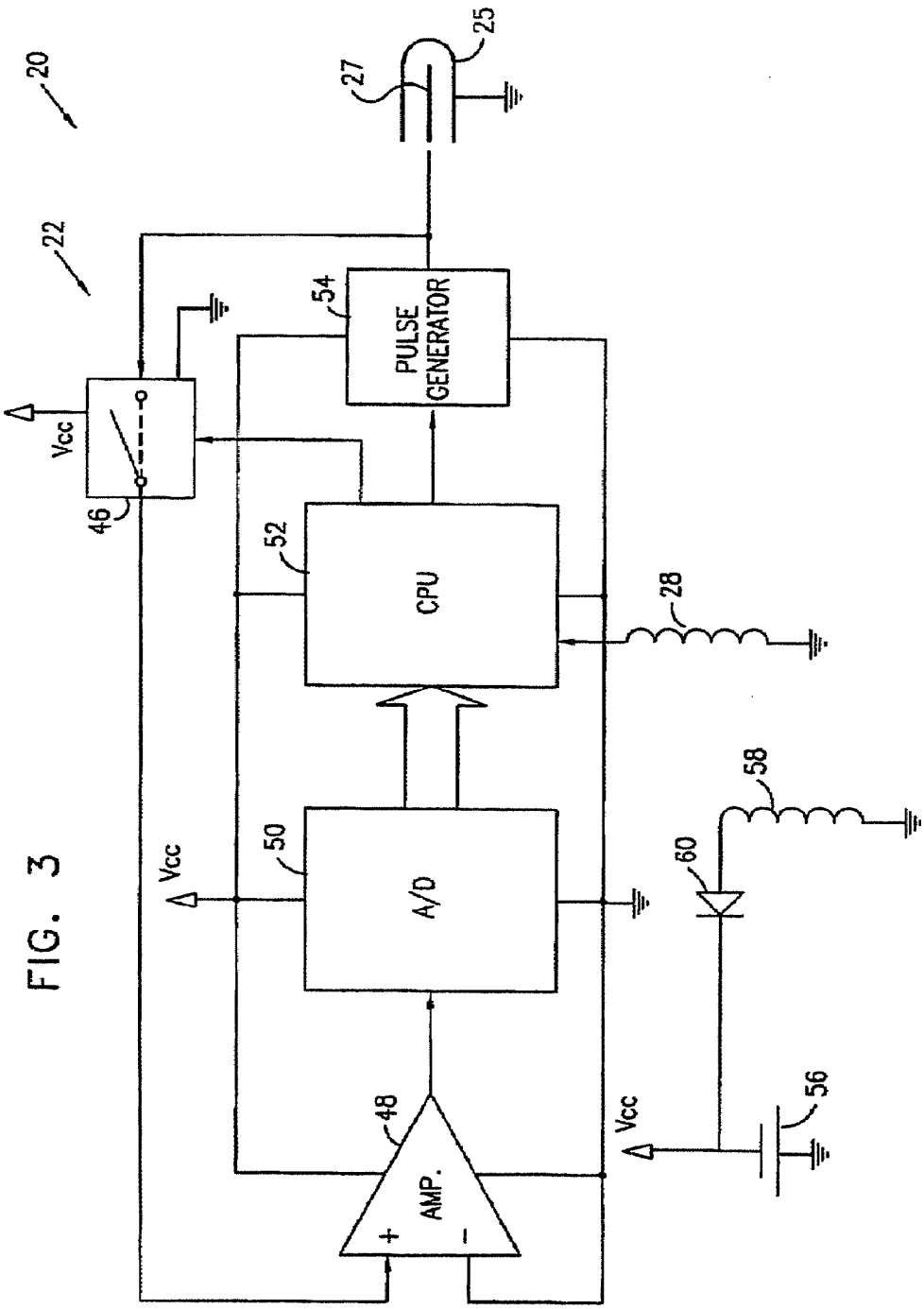
FIG. 3 is a schematic block diagram illustrating circuitry used in an implantable muscle stimulation device, in accordance with a preferred embodiment of the present invention.

FIG. 3 is a schematic block diagram showing circuitry used in control unit 27 to receive signals from and apply electrical waveforms to electrode 27, in accordance with a preferred embodiment of the present invention. Although in this embodiment device 20 is described as operating in a unipolar mode, the principles described hereinbelow are applicable to bipolar operation as well, in which both electrodes 27 and 29 are active.

Electrode 27 receives EMG signals from muscle 32, which are conveyed via a switch 46, which is normally closed, to the input of an amplifier 48, preferably a low-noise operational amplifier. Amplified signals output from amplifier 48 are digitized by an analog/digital (A/D) converter 50 and conveyed to a central processing unit (CPU) 52, preferably a microprocessor. Preferably, although not necessarily, the amplified signals are not rectified prior to being digitized, to allow various forms of analysis, for example, spectral analysis, to be performed on the raw data, without the distortion imparted by rectification. CPU 52 preferably analyzes these signals and/or signals from other physiological sensors, such as ultrasound, pressure, and acceleration sensors described hereinbelow, to determine whether they fit a pattern indicating that incontinence, i.e., involuntary urine flow from bladder 36, is likely to result. The analysis preferably comprises a spectral analysis and an analysis of EMG signal magnitude and rate. Responsive to a determination that incontinence is likely, a pulse generator 54 conveys electrical pulses to electrode 27, as described hereinbelow.

Optionally, sensor 44 comprises a miniaturized ultrasound transducer, which is implanted in proximity to bladder 36. Signals from the transducer are conveyed to control unit 22 for analysis, particularly so as to enable the control unit to estimate the urine volume within the bladder. When, the bladder is empty, there is no need to actuate electrodes 27 and 29, even when a transient increase in the electromyogram (EMG) signal, would otherwise indicate an increased probability of imminent incontinence. Alternatively, the EMG signal itself may be analyzed to gain an indication of the urine volume in the bladder, since when the bladder is full, the average EMG activity typically increases.

The CPU is preferably programmed to distinguish between incontinence-related patterns and other signal patterns not associated with incontinence, such as signals generated when patient 31 wishes to pass urine voluntarily. Preferably, the CPU gathers long-term statistical information regarding the EMG and the signals from the other sensors, and analyzes the information to "lean" common signal patterns that are characteristic of patient 31. The learned patterns are used in refining decision criteria used by the CPU in detecting whether or not to apply waveforms to the electrodes.

(ii) Simulation of a Typical EMG

Figure 6:
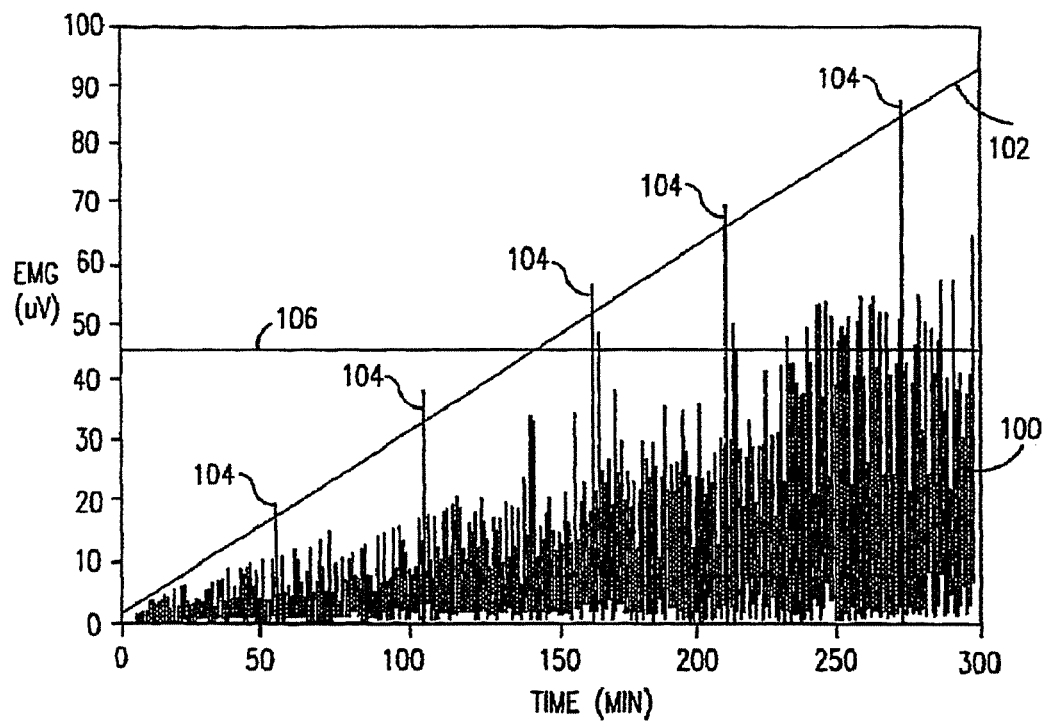
Figure 7:
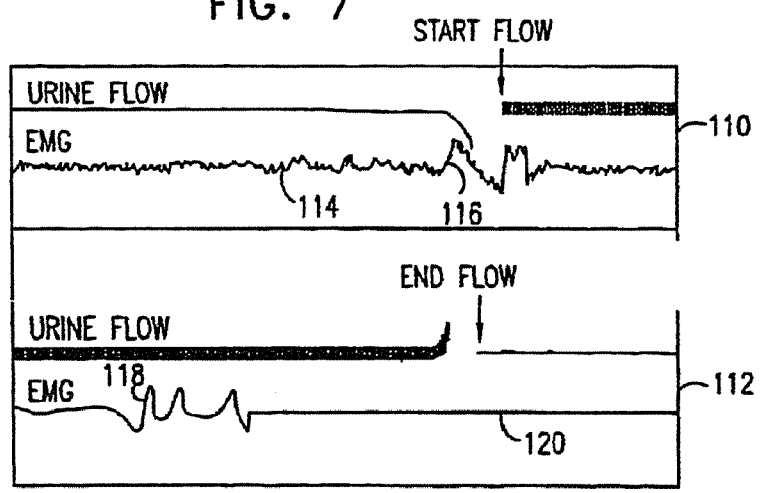

FIG. 6 is a graph that schematically illustrates results of a simulation experiment, in accordance with a preferred embodiment of the present invention, including a simulated EMG signal 100 of a woman suffering from incontinence. A variable, adaptive threshold level 102 is marked on the graph. Over the course of several hours, as the woman's bladder fill level increases, the average level of EMG signal 100 increases accordingly. In this example, threshold level 102 is computed so as to increase as a function of the average EMG. Alternatively or additionally, threshold level 102 and a plurality of other time-varying detection parameters are calculated as functions of other features of the EMG signal or of other aspects of the woman's condition (particularly as measured by sensors 44, 76 and 78 (FIG. 4)), and are used separately or in combination in determining whether to apply stimulation to inhibit involuntary urine flow. Adaptive threshold level 102 enables five possible incidents of incontinence, marked by excursions 104 of signal 100 over level 102, to be detected reliably, with a low false alarm rate. On the other hand, if a fixed threshold level 106 is used, as is known in the art, a number of EMG excursions 104 are missed, and the false alarm rate is high.

(iii) Experimentally Measured EMG Signals: Distinguishing Incontinence from Voluntary Voiding FIG. 7 includes graphs 110 and 112 that schematically illustrate experimental measurements made before, during and after voluntary voiding of urine, in accordance with a preferred embodiment of the present invention. Graph 112 is a continuation in time of graph 110. The upper trace in both graphs illustrates urine flow, wherein the beginning and end of voluntary flow are marketed by arrows. The lower trace illustrates measured EMG signals.

In a period preceding voiding, an EMG signal 114 shows substantial high-frequency activity, which is generally indicative of a full bladder High-frequency spikes in signal 114 (of which none appear in FIG. 7) would be interpreted by CPU 52 as signs of imminent incontinence, leading to actuation of pulse generator 54. On the other hand, voluntary voiding is preceded by an EMG signal 116, in which there is a large but gradual increase in the signal level. Signal 116 is associated with voluntary activation of the pelvic floor muscles for the purpose of passing urine from the bladder, as is a later signal 118 during voiding. Therefore, CPU 52 analyzes not only the level of the EMG signals, but also a rate of change of the signals, in order to distinguish between voluntary and involuntary contractions of the pelvic muscles. When the rate of change is characteristic of voluntary voiding, no stimulation is applied by pulse generator 54.

FIG. 8 (not to scale) includes two graphs, showing: (a) data recorded during a series of periods A, B, C and D, representing stages before, during, and after urination, and (b) preferred times with respect to these periods for activation of pulse generator 54 in order to inhibit urge incontinence, in accordance with a preferred embodiment of the present invention. Bladder pressure data 140 and EMG data 150 shown in FIG. 8 are based on text and a figure in the above-referenced book, *Urinary Incontinence* (p. 35), which describes the voluntary voiding of a healthy adult human female subject. Preferably, inputs to control unit 22 include the EMG data and bladder pressure data, to enable the control unit to determine an appropriate time to activate the pulse generator.

During period A, the bladder fills, which filling is preferably detected and identified as such by the control unit. Notably, in period A there is a slow, steady increase in bladder pressure, as well as a slow, steady increase in peak-to-peak amplitude of the EMS signal. Bladder pressure is seen to increase sharply during voiding period B, in comparison to the slow increase of period A. During period C, voiding was terminated. During period D, the bladder fills in substantially the same manner as in period A, as described. Examination of periods B and C shows that the EMG signal has essentially zero magnitude during voiding and during its termination, and generally increases with increasing bladder pressure during the bladder-filing periods A and D.

Preferably, control unit 22 identifies an initiation time or normal voiding by analysis of the EMG and/or bladder pressure data. In a preferred embodiment, the control unit actuates pulse generator 54 to apply pulses to electrodes 27 and/or 29 at a predetermined time after voiding. For example, in an interview conducted during the calibration period, it may be determined that a particular patient generally only experiences urge incontinence greater than 1.5 hours following voluntary voiding. The control unit may then be programmed to detect voiding and initiate pulse application one hour thereafter, and to continue the pulse application until a subsequent onset of voluntary voiding is detected. Alternatively or additionally, the pulse generator may be actuated by the control unit when the average magnitude of the EMG exceeds a specified threshold. Further alternatively or additionally, the calibration period may include a training period, in which the control unit continually samples the EMG signal, and in which the patient indicates to the control unit whenever urge incontinence occurs. During or subsequent to the training period, the control unit or an external processor (not shown) analyzes each instance of urge incontinence to determine aspects of the EMG signal preceding the incontinence which can be used during regular operation of the unit to predict incontinence. For many applications of the present invention, the control unit is operative to execute each of the above methods, so as to minimize or eliminate occurrences of urge incontinence. It will be appreciated that these strategies may be applied to other types of incontinence as well, mutatis mutandis.

D. Muscle Stimulation

When possible incontinence is detected, CPU 52 opens switch 46 (FIG. 3) and commands pulse generator 54 to apply a suitable electrical waveform to electrode 27 so as to stimulate muscle 32 to contract. Switch 46 is opened in order to avoid feedback of the stimulation waveform to amplifier 48, and is closed again after the waveform is terminated. In the embodiment shown in FIG. 3, the waveform is applied to the electrode in a unipolar mode, wherein a case 25 of control unit 22 serves as the return (ground) electrode. (This mode can be used only when case 25 comprises a conductive material. When control unit 22 has a plastic case, at least two electrodes are generally needed, in order to administer bipolar stimulation.) As muscle 32 contracts, it closes off urethra 34, thus inhibiting the undesired urine flow. Preferably, the waveform is terminated and switch 46 is closed after a predetermined period of time, typically about 5 sec, has passed. If possible incontinence is again detected at this point, the waveform is re-applied.

It will be appreciated that, depending on the particular application, one or more waveforms may be employed in the practice of various embodiments of the present invention. For example, the waveform may be uniphasic or biphasic and may have a range of amplitudes, duty cycles and/or frequencies. It has been found generally that pulse frequencies in the range between 5 and 200 Hz are effective in engendering contraction of the levator ani and other pelvic muscles, but it may also be possible to use frequencies outside this range. In a preferred embodiment, the waveform comprises a bipolar square wave having the following characteristics:

Current 30-100 mA,
Voltage 9-15 V,
Pulse width 0.1-2.0 ms, variable in increments of 0.1 ms, and
Pulse repetition rate 20-50 Hz, preferably 20-30 Hz Alternatively, the waveform may comprise a decaying square wave, sinusoid or sawtooth or have any other shape found to be suitable. Further alternatively or additionally, the waveform may comprise one or more bursts of short pulses, each pulse preferably less than 1 ms in duration. Generally, appropriate waveforms and parameters thereof are determined during the initial test period.

E. Provision of Power to the Control Unit

Power is supplied to the elements of control unit 22 by a battery 56, which may comprise a primary battery (non-rechargeable) and/or a rechargeable battery. Alternatively, a super-capacitor, as is known in the art, may be used to store and provide the electrical power. If a rechargeable battery or super-capacitor is used, it is preferably recharged via an inductive coil 58 or antenna, which receives energy by magnetic induction from an external magnetic field charging source (not shown) held in proximity to the pelvis of patient 31. The magnetic field causes a current to flow in coil 58, which is rectified by a rectifier 60 and furnished to charge battery 56. An optional coil 28, coupled to CPU 52 for the purpose of wireless communications with device 20, may also be used for charging the battery.

Preferably, battery 56 comprises a standard battery, such as a lithium battery, having a nominal output of 3 volts. Most preferably, pulse generator 54 comprises a DC/DC converter, as is known in the art, and a capacitor, which is charged by the DC/DC converter to a constant, stepped-up voltage level regardless of the precise battery voltage, which may vary between 3.5 and 1.8 volts. The same DC/DC converter, or another similar device, preferably supplies power to other circuit components of control unit 22.

F. External Communication with the Control Unit

An inductive arrangement using coil 28, is preferably used to program the CPU, using an external programming device (not shown) with a suitable antenna. Alternatively, the programming device generates a modulated magnetic field to communicate with a receiver inside case 25, which preferably senses the field using a Hall effect transducer. Such programming may be used, for example to set an amplitude or duration of the stimulator waveform applied by pulse generator 54, or to set a threshold level or other parameters, according to which the CPU distinguishes between electromyographic or other signals that are indicative of impending incontinence and those that are not (e.g., those that indicate voluntary voiding). Such programming may be carried out by medical personnel or by the patient herself, who can similarly turn the implanted control unit on and off as desired by passing a suitable magnet over the area of her pelvis.

Although the circuit blocks in control unit 22 are shown as discrete elements, some or all of these blocks are preferably embodied in a custom or semi-custom integrated circuit device, as is known in the art.

G. Utilization of Other Sensors

Figure 4:
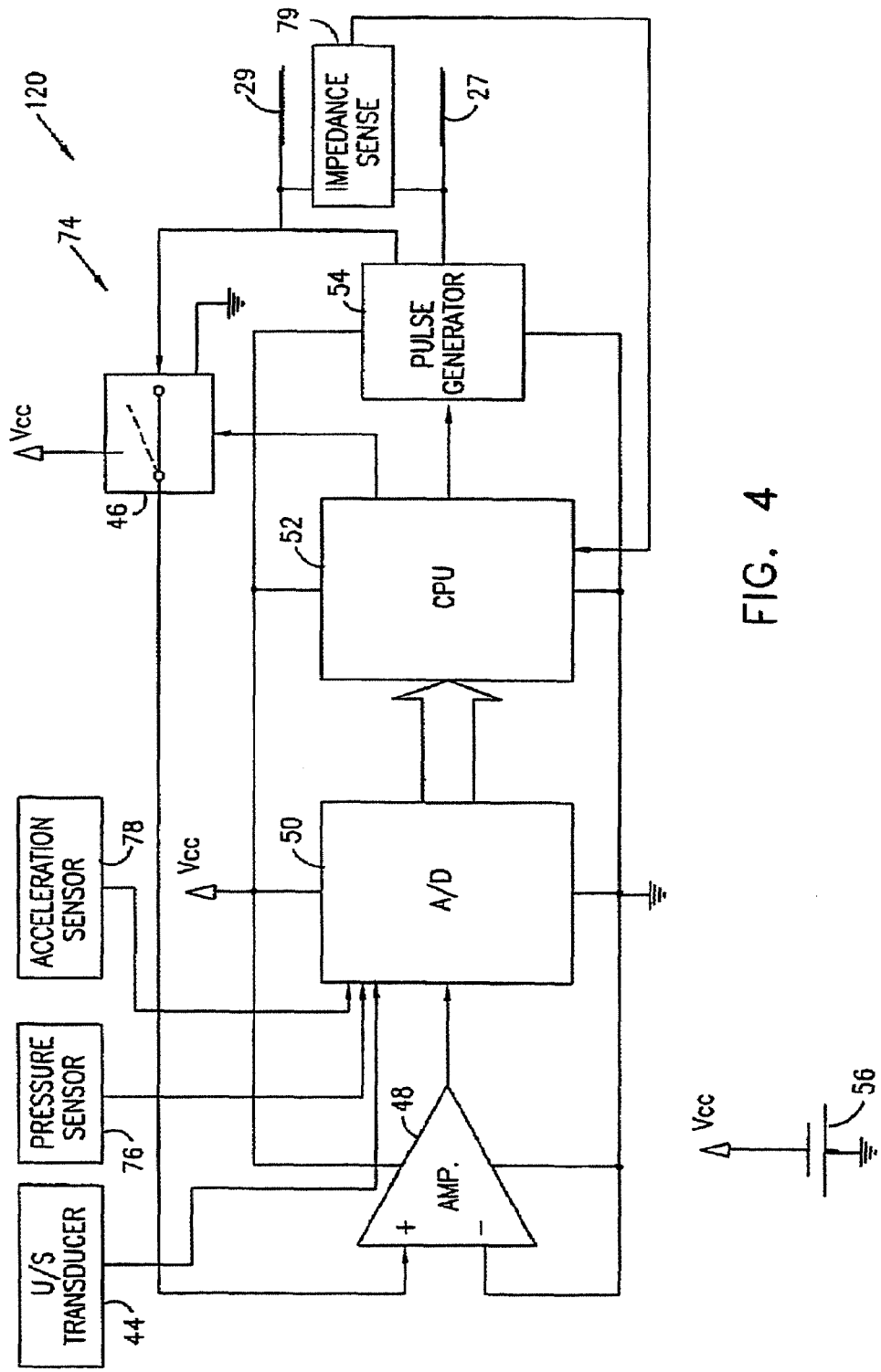
FIG. 4 is a schematic block diagram illustrating circuitry used in an implantable muscle stimulation device, in accordance with another preferred embodiment of the present invention.

FIG. 4 is a schematic block diagram illustrating a muscle stimulator device 120, in accordance with an alternative embodiment of the present invention. Device 120 is substantially similar to device 20, except for features descried hereinbelow. Device 120 comprises a control unit 74, which is coupled to electrodes 27 and 29. Electrode 29 also serves as a sensing electrode, furnishing electromyographic signals via switch 46 to amplifier 48, as described hereinabove. Alternatively, electrodes 27 and 29 may be coupled as differential inputs to amplifier 4. Pulse generator 54 applies the stimulation waveforms between electrodes 27 and 29 in a bipolar mode.

In addition to or instead of the electromyographic signals received from electrode 29, CPU 52 preferably receives additional signals from other physiological sensors, such as ultrasound transducer 44 (shown in FIG. 2), a pressure sensor 76 and/or an acceleration sensor 78, or other types of strain and motion measurement devices, as are known in the art. Pressure sensor 76 is preferably implanted on or in bladder 36, so as to detect increases in abdominal or intravesical pressure that may lead to involuntary urine loss. Similarly, acceleration sensor 78 is preferably implanted so as to detect bladder motion associated with hypermobility, which is similarly associated with urine loss. The additional signals from these sensors are preferably analyzed by the CPU together with the electromyographic signals in order to improve the accuracy and reliability of detection of impending incontinence.

An impedance sensor 79 is preferably used to measure the tissue impedance between leads 27 and 29, using physiological impedance measurement techniques known in the art. During long-term use of device 120 (or other such devices), fibrosis in the area of the implanted electrodes tends to cause the impedance to increase, so that the stimulating current for a given applied voltage decreases. The impedance measured by sensor 79 is used as a feedback signal instructing CPU 52 to increase the voltage, so that a generally constant level of stimulation current is maintained.

H. Reduction of Power Consumption

Figure 5:
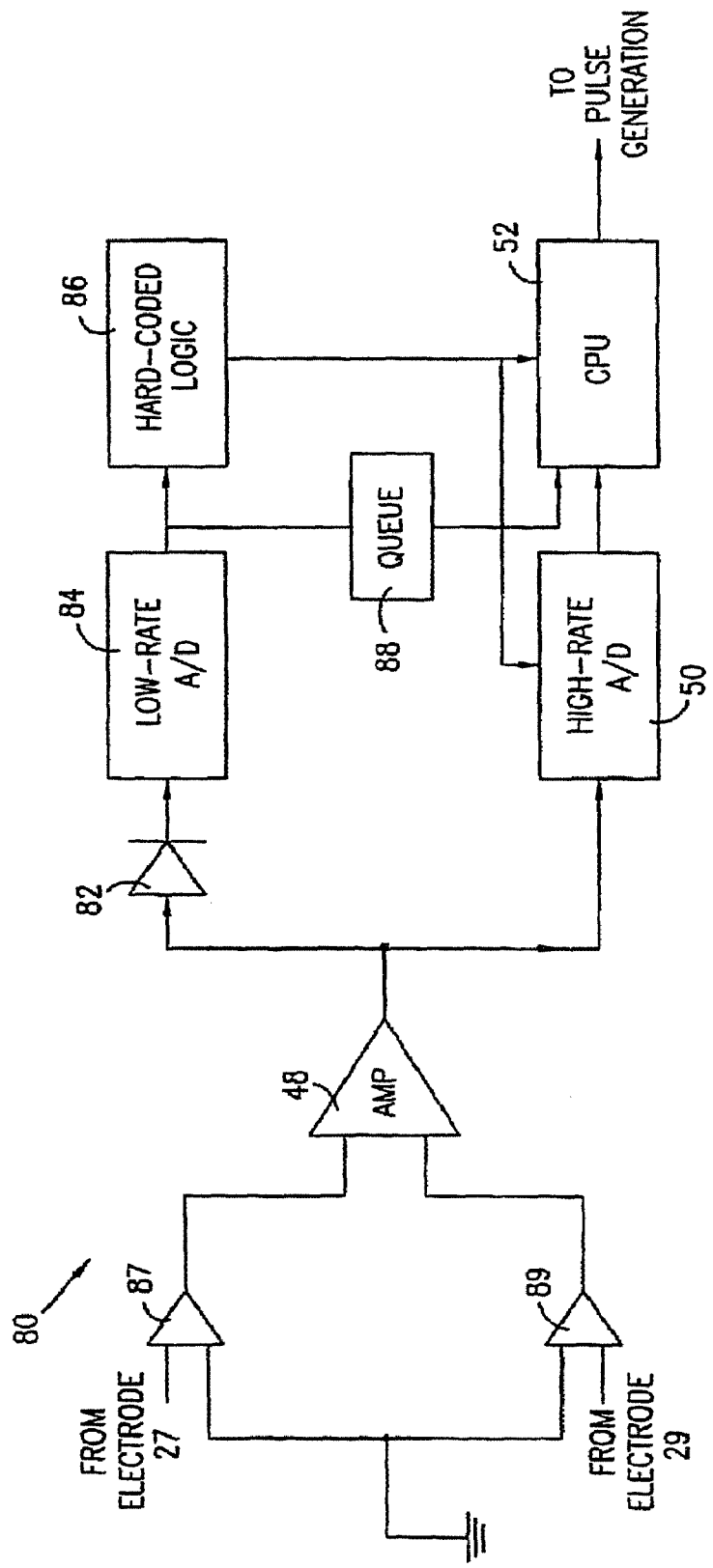
FIG. 5 is a schematic block diagram illustrating signal processing circuitry for analyzing electromyogram signals, in accordance with a preferred embodiment of the present invention.

FIG. 5 is a schematic block diagram showing details of signal processing circuitry 80 for use in device 20 or 120, in accordance with a preferred embodiment of the present invention. In order to detect impending incontinence with adequate reliability, A/D converter 50 optimally samples the EMG signals from the electrodes at 1000-5000 Hz, and CPU 52 preferably performs a detailed analysis of the sample stream. Systems for incontinence control known in the art, operating at sample rates below 1000 Hz, cannot adequately distinguish between signals that may be indicative of incontinence and those that are not. For the purpose of such high-rate sampling, CPU 52 preferably comprises a low-power, software-programmable processor. If A/D converter 50 and CPU 52 were to operate continuously, however, battery 56 would rapidly run down. Therefore, circuitry 80 comprises a low-power, low-resolution A/D converter 84 and hard-coded processing logic 86, which operate continuously at a low sampling rate, preferably at about 100-200 Hz. Input from amplifier 48 to A/D converter 84 is preferably rectified by a rectifier 82.

In operation, A/D converter 50 and CPU 52 are normally maintained in a standby state, in which their power consumption is negligible. When logic 86, operating at the low sampling rate, detects EMG signals that may be a precursor to incontinence, it signals A/D converter 50 to begin sampling at the high rate. In order nor to lose significant data from the brief period before A/D converter 50 and CPU 52 turn on, signals from A/D converter 84 are preferably stored in a cyclic (or first-in first-out) queue 88, such as a delay line. The entire sequence of signal detection and processing is estimated to take between 5 and 20 ms, up to the point at which CPU 52 reaches a decision as to whether or not to actuate pulse generator 54. Pulse generation takes between 1 and 20 ms, with the result that contraction of the pelvic muscles begins within 15-50 ms of the onset of increased EMG activity indicating impending urine loss. Thus, urethra 34 is substantially closed off before any significant amount of urine can leak out.

As shown in FIG. 5, EMG inputs from electrodes 27 and 29 are preferably amplified before processing in a dual-differential configuration, so as to afford enhanced sensitivity and reduced noise. Electrodes 27 and 29 are coupled to respective differential preamplifiers 87 and 89, the outputs of which are differentially amplified by amplifier 48.

Although preferred embodiments of the present invention are described hereinabove with reference to treatment of urinary urge incontinence, it will be appreciated that the principles of the present invention may be applied as well to treat other types of incontinence, such as stress incontinence, and to treat and enhance the function of other muscles in the body.

It will be appreciated by persons skilled in the an that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

The invention claimed is:

1. A method comprising:
   implanting at least one electrode in a patient in contact with a pelvic muscle of the patient;
   implanting a stimulator device in the patient; and
   driving the at least one electrode to apply a biphasic electrical waveform to the muscle using the stimulator device.

2. The method according to claim 1, wherein implanting the at least one electrode comprises implanting the at least one electrode in the pelvic muscle.

3. The method according to claim 1, further comprising contracting the pelvic muscle in response to driving the at least one electrode, wherein urine flow through a urethra of the patient is inhibited.

4. The method according to claim 3, wherein driving the at least one electrode comprises configuring the waveform to treat urinary urge incontinence.

5. The method according to claim 3, wherein driving the at least one electrode comprises configuring the waveform to treat stress incontinence.

6. A method comprising:
   implanting at least one elongated electrode structure in contact with a pelvic muscle of the patient;
   implanting a stimulator device in the patient;
   driving the at least one electrode to apply an electrical waveform to the muscle using the stimulator device;
   providing for the electrical waveform a plurality of pulses each having pulse width duration of 2 ms or less; and
   contracting the pelvic muscle in response to driving the at least one electrode, wherein urine flow through the urethra of the patient is inhibited.

7. The method according to claim 6, wherein implanting the at least one electrode comprises implanting the at least one electrode in the pelvic muscle.

8. The method according to claim 6, wherein providing for the electrical waveform comprises setting the pulse width durations of the pulses within a range of 0.1 ms to 2 ms.

9. The method according to claim 6, wherein the plurality of pulses each have a pulse width duration of less than 1 ms.

10. The method according to claim 6, wherein driving the at least one electrode comprises configuring the waveform to treat urinary urge incontinence.

11. The method according to claim 6, wherein driving the at least one electrode comprises configuring the waveform to treat stress incontinence.

12. The method according to claim 6, wherein the pelvic muscle includes the levator ani muscle, and wherein implanting the at least one electrode comprises implanting the at least one electrode in the levator ani muscle.

13. The method according to claim 6, wherein the pelvic muscle includes the urethral sphincter muscle, and wherein implanting the at least one electrode comprises implanting the at least one electrode in the urethral sphincter muscle.

14. The method according to claim 6, further comprising terminating application of the waveform to the muscle after a predetermined period of time.

15. The method according to claim 14, wherein the predetermined period of time is about 5 seconds.

16. The method according to claim 14, wherein driving the at least one electrode comprises driving the at least one electrode to reapply the waveform after termination of the application of the waveform.

17. The method according to claim 6, wherein driving the at least one electrode comprises providing for the waveform a biphasic electrical waveform.

* * * * *

UNITED STATES PATENT AND TRADEMARK OFFICE
CERTIFICATE OF CORRECTION

PATENT NO. : 7,582,053 B2  
APPLICATION NO. : 10/671144  
DATED : September 1, 2009  
INVENTOR(S) : Gross et al.

Page 1 of 1

It is certified that error appears in the above-identified patent and that said Letters Patent is hereby corrected as shown below:

On the Title Page,
Item [56] References Cited change:
"Vicent" to --Vincent--.

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,582,053 B2 Page 1 of 1
APPLICATION NO. : 10/671144
DATED : September 1, 2009
INVENTOR(S) : Gross et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1281 days.

Signed and Sealed this

Fourteenth Day of September, 2010

David J. Kappos
*Director of the United States Patent and Trademark Office*